(12) United States Patent
Sandrin

(10) Patent No.: US 11,160,531 B2
(45) Date of Patent: Nov. 2, 2021

(54) ULTRASOUND PROBE WITH HOUSING AND INTERCHANGEABLE TIP

(71) Applicant: ECHOSENS, Paris (FR)

(72) Inventor: Laurent Sandrin, Bourg-la-Reine (FR)

(73) Assignee: ECHOSENS, Paris (FR)

( * ) Notice: Subject to any disclaimer, the term of this patent is extended or adjusted under 35 U.S.C. 154(b) by 542 days.

(21) Appl. No.: 15/576,071

(22) PCT Filed: May 23, 2016

(86) PCT No.: PCT/EP2016/061559
§ 371 (c)(1),
(2) Date: Nov. 21, 2017

(87) PCT Pub. No.: WO2016/188947
PCT Pub. Date: Dec. 1, 2016

(65) Prior Publication Data
US 2018/0140274 A1     May 24, 2018

(30) Foreign Application Priority Data

May 22, 2015   (EP) .................................... 15168841

(51) Int. Cl.
*A61B 8/00*     (2006.01)
*A61B 8/08*     (2006.01)
(52) U.S. Cl.
CPC .......... *A61B 8/4411* (2013.01); *A61B 8/4455* (2013.01); *A61B 8/485* (2013.01); *A61B 8/56* (2013.01); *A61B 8/4438* (2013.01); *A61B 8/585* (2013.01)

(58) Field of Classification Search
CPC ... A61B 8/4411; A61B 8/4438; A61B 8/4455; A61B 8/485; A61B 8/56; A61B 8/585; A61B 8/4444
See application file for complete search history.

(56) References Cited

U.S. PATENT DOCUMENTS

| 5,402,793 A | 4/1995 | Gruner et al. |
| 6,338,716 B1 | 1/2002 | Hossack et al. |
| 6,500,126 B1 | 12/2002 | Brock-Fisher |

(Continued)

FOREIGN PATENT DOCUMENTS

| CN | 202 600 740 U | 12/2012 |
| EP | 2 837 949 A1 | 2/2015 |

(Continued)

OTHER PUBLICATIONS

International Search Report as issued in International Patent Application No. PCT/EP2016/061559, dated Aug. 4, 2016.

(Continued)

*Primary Examiner* — Carolyn A Pehlke
(74) *Attorney, Agent, or Firm* — Pillsbury Winthrop Shaw Pittman LLP

(57) ABSTRACT

An interchangeable tip for ultrasound probe housing includes: at least one ultrasound transducer constructed and configured to emit and receive ultrasound signals, at least one electrical contact of tip, each electrical contact of tip being constructed and configured to cooperate with an electrical connector, a tip connector constructed and configured to secure the interchangeable tip with an ultrasound probe housing.

23 Claims, 3 Drawing Sheets

(56) References Cited

U.S. PATENT DOCUMENTS

| | | |
|---|---|---|
| 2003/0036702 A1 | 2/2003 | Davidsen |
| 2004/0002658 A1 | 1/2004 | Marian |
| 2010/0191123 A1* | 7/2010 | Tsung ................... A61B 8/445 |
| | | 600/463 |
| 2010/0249598 A1 | 9/2010 | Smith et al. |
| 2013/0225993 A1 | 8/2013 | Takahashi |
| 2015/0032004 A1* | 1/2015 | Kim ..................... A61B 8/4438 |
| | | 600/443 |

FOREIGN PATENT DOCUMENTS

| | | |
|---|---|---|
| FR | 2 843 290 A1 | 2/2004 |
| KR | 10-2013-0080985 A | 7/2013 |

OTHER PUBLICATIONS

Examination Report as issued in Brazilian Patent Application No. BR112017024865-4, dated Jul. 31, 2020.

* cited by examiner

ULTRASOUND PROBE WITH HOUSING AND INTERCHANGEABLE TIP

CROSS-REFERENCE TO RELATED APPLICATIONS

This is the U.S. National Stage of PCT/EP2016/061559, filed May 23, 2016, which in turn claims priority to European Patent Application No. 15168841.3, filed May 22, 2015, the entire contents of all applications are incorporated herein by reference in their entireties.

FIELD OF THE INVENTION

The present invention relates generally to an interchangeable tip for ultrasound probe adapted and constructed for transient elastography.

BACKGROUND OF THE INVENTION

Transient elastography (or Vibration-Controlled Transient Elastography) is a non-invasive method for assessing liver stiffness using an ultrasound probe. The ultrasound probe comprises an ultrasound transducer adapted to emit and receive ultrasound signals in pulse echo mode. Ultrasound signals are acquired and used to follow the propagation of shear waves inside an organ such as the liver. In transient elastography, the characteristics of the ultrasound probe may be adapted to body morphology. More particularly, children or small adult livers are measured with a first type of ultrasound probe implementing an ultrasound transducer comprising a diameter of 5 mm and having a central frequency of 5 MHz, adult livers are measured with a second type of ultrasound probe implementing an ultrasound transducer comprising a diameter of 7 mm and having a central frequency of 3.5 MHz, and obese adult livers are measured with a third type of ultrasound probe implementing an ultrasound transducer comprising a diameter of 10 mm and having a central frequency of 2.5 MHz. Therefore, in transient elastography the probe should be adapted to patient morphology. If only one probe with one type of ultrasound transducer is used for all morphologies, the performance is significantly lower. For example, the success rate on obese human is significantly improved with a probe comprising an ultrasound transducer comprising a diameter of 10 mm and having a central frequency of 2.5 MHz.

Therefore, several ultrasound probes equipped with different ultrasound transducers are being used which is complex for the operator who can have easily three types of ultrasound probes to manipulate and organize in his setting.

SUMMARY

An aspect of the invention is directed to an interchangeable tip for ultrasound probe housing that overcomes the aforementioned drawbacks. Accordingly, an embodiment of the invention is directed to an interchangeable tip for an ultrasound probe housing allowing to be plugged on the ultrasound probe housing.

To achieve this, an aspect of the present invention is directed to an interchangeable tip for ultrasound probe housing comprising:
At least one ultrasound transducer constructed and configured to emit and receive ultrasound signals,
At least one electrical contact of tip, said electrical contact of tip being constructed and configured to cooperate with an electrical connector,
A tip connector constructed and configured to secure the interchangeable tip with an ultrasound probe housing.

Another aspect of the present invention is an ultrasound probe comprising an interchangeable tip and an ultrasound probe housing, said interchangeable tip comprising:
At least one ultrasound transducer constructed and configured to emit and receive ultrasound signals,
At least one electrical contact of tip, said electrical contact of tip being constructed and configured to cooperate with an electrical connector,
A tip connector constructed and configured to secure the interchangeable tip with an ultrasound probe housing,
Wherein said ultrasound probe housing is characterized in that it comprises:
A probe housing connector constructed and configured to cooperate with the tip connector of the interchangeable tip,
An electrodynamic actuator constructed and configured to cooperate with the at least one ultrasound transducer, said electrodynamic actuator being adapted to generate a low frequency impulse having a frequency range between about 1 Hz and about 5000 Hz.

Therefore, the operator can have only a unique ultrasound probe housing with multiple interchangeable tips, each interchangeable tip being specific to a body type, for example children, adult or obese.

In a non-limiting embodiment, the interchangeable tip is constructed and configured to embed at least one electronic component connected to at least one electrical contact of tip suitable to cooperate with an electrical connector.

In a non-limiting embodiment, the electronic component is a memory suitable to store data relative to the interchangeable tip.

In a non-limiting embodiment, the memory is a one wire EEPROM chip connected to three electrical contacts of tip, two electrical contacts of tip being used for the ultrasound transducer and one electrical contact of tip for the EEPROM chip.

In a non-limiting embodiment, the electronic component is a RFID chip suitable to store the interchangeable tip identity information. In a non-limiting embodiment, the electronic component is an acceleration sensor.

In a non-limiting embodiment, the interchangeable tip comprises a first magnet constructed and configured to cooperate with the ultrasound probe housing.

In a non-limiting embodiment, the interchangeable tip comprises a first keying device constructed and configured to cooperate with a second keying device of an ultrasound probe housing.

In a non-limiting embodiment, the tip connector is formed by a screw thread constructed and configured to cooperate with a screw thread of an ultrasound probe housing.

An aspect of the invention relates also to an ultrasound probe housing comprising a probe housing connector constructed and configured to cooperate with the tip connector of the interchangeable tip according to the invention.

In a non-limiting embodiment, the probe housing connector is formed by a screw thread constructed and configured to cooperate with the screw thread of the tip connector.

In a non-limiting embodiment, the ultrasound probe housing comprises a second keying device constructed and configured to cooperate with the first keying device of the interchangeable tip.

In a non-limiting embodiment, the ultrasound probe housing comprises a second magnet constructed and configured to cooperate with the interchangeable tip.

In a non-limiting embodiment, the ultrasound probe housing comprises an electrodynamic actuator constructed and configured to cooperate with the at least one ultrasound transducer that generates a low-frequency impulse having a frequency range between about 1 Hz and about 5000 Hz.

In a non-limiting embodiment, the ultrasound probe housing comprises at least one electrical contact of probe suitable to cooperate with an electrical connector.

In a non-limiting embodiment, the ultrasound probe housing comprises at least one processor.

In a non-limiting embodiment, the ultrasound probe housing comprises reading means constructed and arranged to communicate with an external processor.

An aspect of the invention relates also to an ultrasound probe comprising an interchangeable tip according to the invention and an ultrasound probe housing according to the invention, the interchangeable tip being secured to the ultrasound probe housing via the interchangeable tip connector and the ultrasound probe housing connector.

In a non-limiting embodiment, the ultrasound probe comprises at least one electronic connector connected at a first end to an electrical contact of the tip and at a second end to an electrical contact of probe housing.

In a non-limiting embodiment, the electronic connector is a spring-loaded connector or a jack like cylindrical connector.

In a non-limiting embodiment the ultrasound probe comprises storing means suitable to store data relative to the interchangeable tip and the ultrasound probe housing comprises reading means configured to scan the storing means and to transmit the tip data to a processor. Storing means are for example a memory or a RFID chip.

Tip data means data relative to tip identity and/or acquisition parameters. In a non-limiting embodiment the storing means comprise a memory and/or a RFID chip.

In a non-limiting embodiment the processor selects the acquisition parameters according to the tip information retrieved from the storing means.

In a non-limiting embodiment the acquisition parameters selected by the processor are chosen from a list comprising the following parameters: the measurement depth, the ultrasound frequency, the shear wave excitation frequency, the shear wave excitation amplitude.

An aspect of the invention relates also to a method of embodying an ultrasound probe according to the invention, the method comprising:
- When an interchangeable tip is secured to the ultrasound probe housing, a step of identifying the interchangeable tip by reading the content of the memory, the reading being implemented by reading means of the ultrasound probe housing,
- When the interchangeable tip secured to the ultrasound probe housing is identified, a step of selecting the acquisition parameters, the selection being implemented by a processor communicating with the ultrasound probe housing.

In a non-limiting embodiment, the method further comprising when the interchangeable tip is removed from the ultrasound probe housing, a step of freezing the acquisition.

In a non-limiting embodiment, the method further comprising when a tip operation threshold is reached by the interchangeable tip, a step of stopping the work of the interchangeable tip.

In a non-limiting embodiment the acquisition parameters selected by the processor are chosen from a list comprising the following parameters: the measurement depth, the ultrasound frequency, the shear wave excitation frequency, the shear wave excitation amplitude.

BRIEF DESCRIPTION OF THE DRAWINGS

The accompanying drawings are included to provide a further understanding of the invention and are incorporated in and constitute a part of this specification, to illustrate embodiments of the invention and, together with the description, to explain the principles of the invention.

DESCRIPTION OF SPECIFIC EMBODIMENTS

Figure 1:
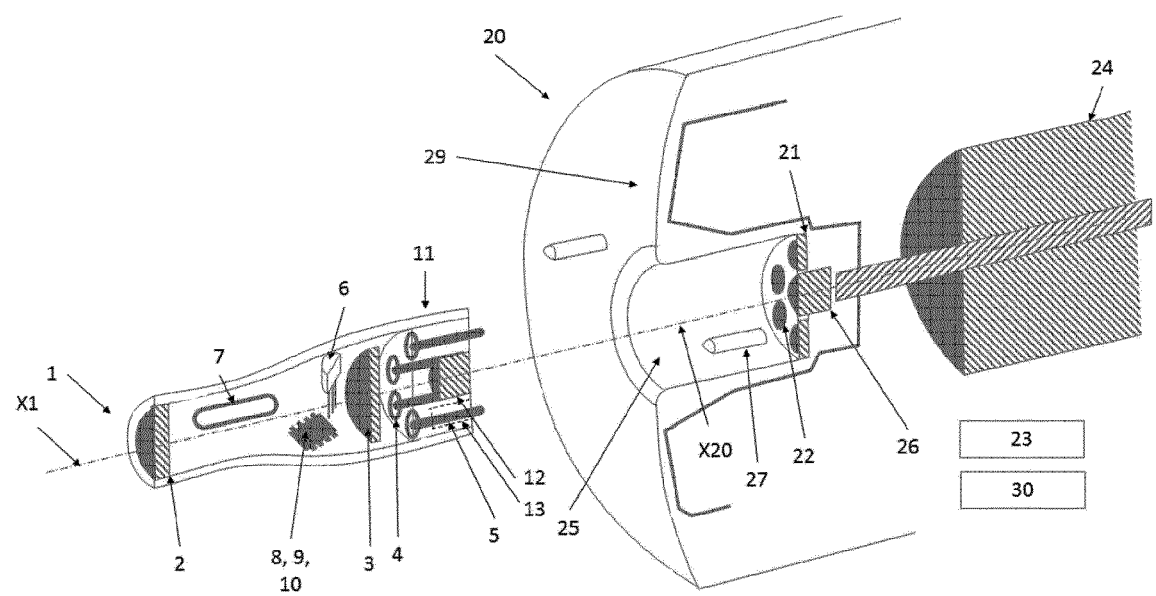
FIG. 1 represents an interchangeable tip for an ultrasound probe housing according to the invention and also an ultrasound probe housing according to the invention.
Figure 2:
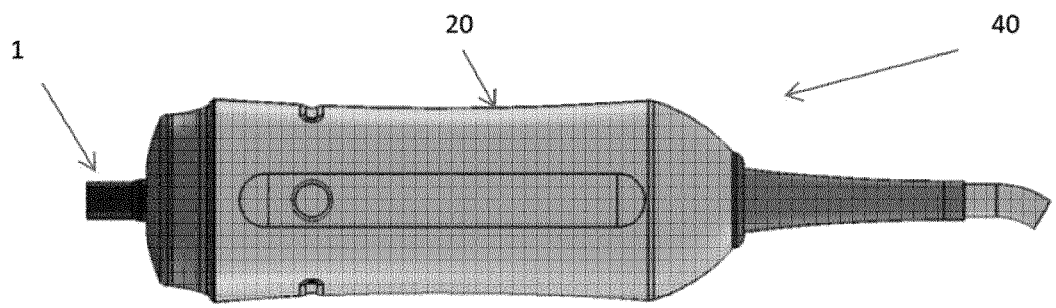
FIG. 2 depicts an ultrasound probe according to the invention.

In reference to FIG. 1, an interchangeable tip 1 for an ultrasound probe housing is represented. In addition, the FIG. 1 depicts an ultrasound probe housing 20 constructed and configured to cooperate with the interchangeable tip 1. An ultrasound probe 40 (See FIG. 2) is formed when the interchangeable tip 1 and the probe housing 20 cooperate themselves.

In a non-limiting embodiment, the interchangeable tip 1 and the ultrasound probe housing 20 may be dedicated to the field of transient elastography for measuring the elasticity of a human or animal organ.

In this non-limiting embodiment, the interchangeable tip 1 comprises one ultrasound transducer 2 constructed and configured to emit and receive ultrasound signals. For example, the ultrasound transducer 2 may be chosen from any of the following ultrasound transducers:

- Ultrasound transducer of 8.0 MHz center frequency of typical diameter 3 mm,
- Ultrasound transducer of 5.0 MHz center frequency of typical diameter 5 mm, this interchangeable tip equipped with this type of ultrasound transducer may be used for measuring the elasticity of children or small adult livers,
- Ultrasound transducer of 3.5 MHz center frequency of typical diameter 7 mm, this interchangeable tip equipped with this type of ultrasound transducer may be used for measuring the elasticity of adult livers
- Ultrasound transducer of 2.5 MHz center frequency of typical diameter 10 mm, this interchangeable tip equipped with this type of ultrasound transducer may be used for measuring the elasticity of obese adult livers, or
- Ultrasound transducer of 1.5 MHz center frequency of typical diameter 12 mm.

Figure 3:
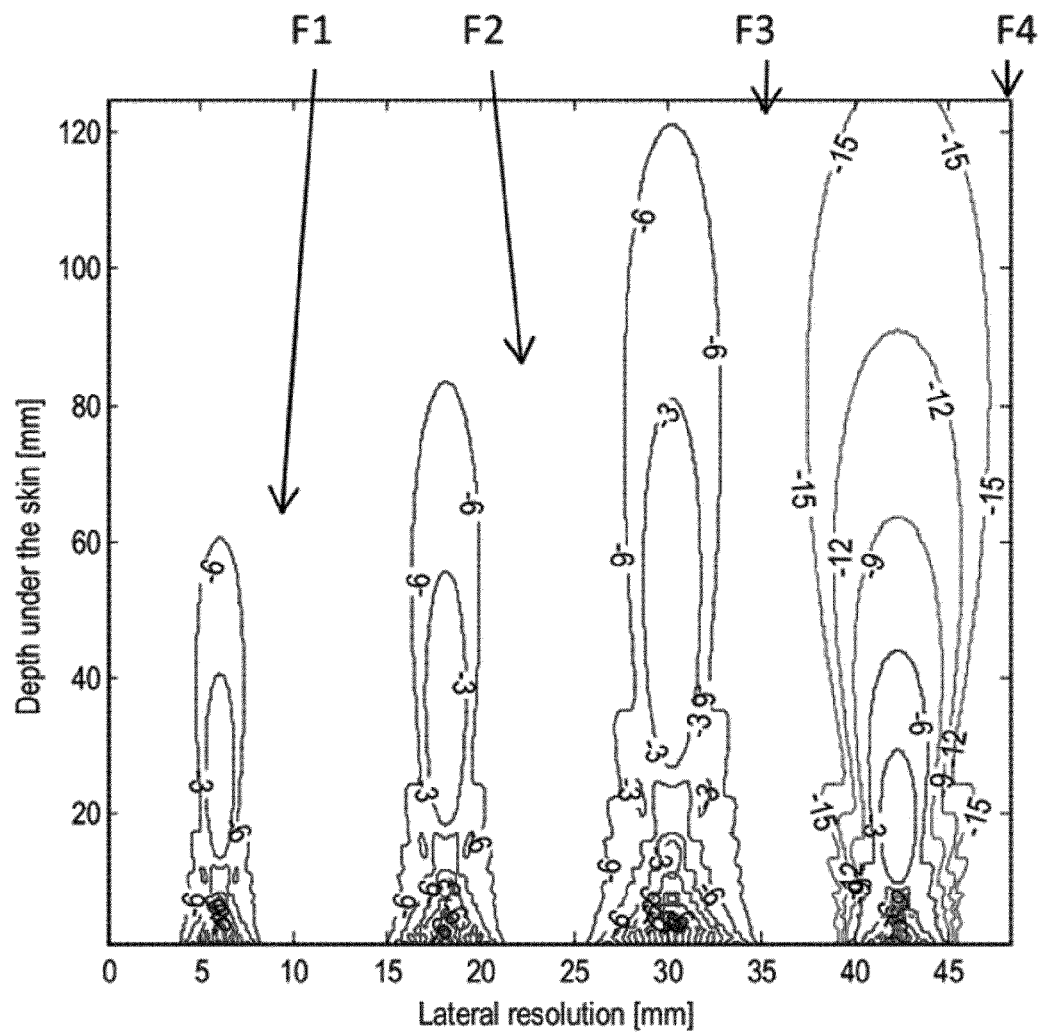
FIG. 3 depicts the diffraction fields of four types of ultrasound transducer.

The FIG. 3 illustrates the diffraction fields of four types of ultrasound transducer.

The diffraction field F1 of an ultrasound transducer of 5.0 MHz center frequency of typical diameter 5 mm is illustrated.

The diffraction field F2 of an ultrasound transducer of 3.5 MHz center frequency of typical diameter 7 mm is represented.

The diffraction field F3 of an ultrasound transducer of 2.5 MHz center frequency of typical diameter 10 mm is illustrated.

The diffraction field F4 of an ultrasound transducer of 1.5 MHz center frequency of typical diameter 10 mm is illustrated.

It appears from FIG. 3 that a unique ultrasound transducer does not permit to realize measurements of different depths under the skin. For instance, with a transducer of typical diameter of 5 mm, the measurements may be realized on a maximal depth under the skin of 60 mm.

When the probe is used to measure the liver of an obese human, a layer of adipose tissue is localized between the skin and the liver. The layer may be of 60 mm. Therefore, a human obese may not efficiently measured with a ultrasound probe equipped with a ultrasound transducer of typical diameter of 5 mm. The measurement will be realized into the adipose tissue and not into the region of interest, in the example, the liver.

Further, the interchangeable tip 1 is constructed and configured to receive electronic components. Further, in the non-limiting embodiment the interchangeable tip 1 comprises several electrical contacts 4 of tip, each electrical contact 4 of tip being connected to an electrical connector 5. These electronic components and electrical contacts 4 may be placed on a PCB 3 of the interchangeable tip.

Electrical connectors 5 are used to electrically connect the electrical contacts 4 of the interchangeable tip and the electrical contacts 22 of the ultrasound probe housing. Electrical connectors 5 may be placed either in the interchangeable tip 1, or in the ultrasound probe housing 20 or in both. An electrical connector 5 may be formed by a standard connector or by a spring-loaded or by a jack-like cylindrical connector By complementarity, the ultrasound probe housing 20 comprises several electrical contacts 22 of probe constructed and configured to match with the several electrical connectors 5 when an interchangeable tip 1 is plugged on the ultrasound probe housing 20. These electrical contacts 22 of probe may be placed on a PCB 21 of the ultrasound probe housing 20.

For example, at least one electrical connector 5 is constructed and configured to transmit signals to and from the ultrasound transducer 2 and possibly other signals to the PCB 21 of the ultrasound probe housing 20. For example, the others signals may be formed by electrical shielding, memory power supply, and/or memory data signals.

In a non-limiting embodiment, the interchangeable tip 1 comprises a memory 6 to store data relative to tip operation, for example the number of measurements performed with the interchangeable tip 1. The memory 6 is located in the interchangeable tip 1, for example embedded on the PCB 3 of the interchangeable tip, and is advantageous as it reduces the number of wires between the interchangeable tip 1 and the ultrasound probe housing 20. In the embodiment, one of the electrical connector 5 is constructed and configured to receive memory power supply from the ultrasound probe housing 20 and possibly other signals.

In a non-limiting embodiment, the memory 6 is a standard EEPROM chip. For example, the memory 6 is an I2C EEPROM requiring 4 electric connectors 5 for the transmission of data, clock, power supply and ground.

In a non-limiting embodiment, the memory 6 is a one wire EEPROM chip. The use of a one-wire EEPROM chip allows reducing the number of electrical connectors 5 and therefore the complexity of the interchangeable tip design. In a non-limiting embodiment, the interchangeable tip 1 or the probe housing 20 comprises three electrical connectors 5, two electrical connectors 5 being used for the ultrasound transducer 2 and one electrical connector 5 for a one wire EEPROM chip.

In a non-limiting embodiment, the interchangeable tip 1 comprises a memory 6 and/or a RFID (for Radio-frequency identification) chip 7 to store the interchangeable tip 1 identity information, such as the manufacturing date, the serial number, the ultrasound frequency of the ultrasound transducer 2 and/or the diameter of the ultrasound transducer 2. The RFID chip 7 may also be embedded on the PCB 3 of the interchangeable tip. Memory 6 and/or RFID chip 7 are defined as storing means 6,7. Storing means 6,7 are used for the purposes of automatically identifying the type of interchangeable tip 1. For example, when an interchangeable tip 1 is connected to the ultrasound probe housing 20, reading means 23 implemented on the PCB 21 of the ultrasound probe housing communicating with a processor 30 are suitable to detect the type of the interchangeable tip 1 connected. The processor 30 may be implemented in the ultrasound probe housing or may be external.

In a non-limiting embodiment, the interchangeable tip 1 comprises an acceleration sensor 8. The acceleration sensor 8 may also be embedded on the PCB 3 of the interchangeable tip. When the interchangeable tip 1 comprises an acceleration sensor 8, the ultrasound probe housing 20 comprises an electrodynamic actuator 24 such as when the interchangeable tip 1 cooperates with the ultrasound probe housing 20 the electrodynamic actuator 24 is attached to the ultrasound transducer 2 and is suitable to generate a transitory low-frequency impulse having a frequency range comprised between about 1 Hz and 5000 Hz. Therefore, the acceleration sensor 8 permits to measure the acceleration during the generation of the transitory low-frequency impulse such as to control the frequency. The control may be realized by the processor 30.

In a non-limiting embodiment, the interchangeable tip 1 comprises a shock sensor 9. The shock sensor 9 may be embedded on the PCB 3 of the interchangeable tip and permits to detect shocks that may damage the interchangeable tip 1.

In a non-limiting embodiment, the interchangeable tip 1 comprises means 10 to control the life expectancy of the interchangeable tip 1. For example, the expectancy depends of the number of exams realized. The means 10 may be embedded on the PCB 3 of the interchangeable tip.

The interchangeable tip 1 comprises also a tip connector 11 constructed and configured to secure the interchangeable tip 1 with the probe housing 20. The tip connector 11 may be formed by a screw thread, or a deformable cylinder.

Besides, the ultrasound probe housing 20 comprises a probe housing connector 25 constructed and configured to cooperate with the tip connector 11. Therefore, when the tip connector 11 is formed by a screw thread, then the probe housing connector 25 is also formed by a screw thread and is constructed and configured to cooperate with the screw thread of the tip connector 11.

In such an embodiment (i.e when the tip connector 11 is formed by a screw thread and the probe housing connector is also formed by a screw), an electrical axisymmetric connection between the electrical contacts 4 of the ultrasound tip 1 and the electrical contacts 22 of the probe is implemented. Therefore, in this embodiment, either the electrical contacts 4 of the ultrasound tip 1 or the electrical contacts 22 of the probe are asymmetrical.

In another embodiment, when the tip connector 11 is formed by a deformable cylinder, then the probe housing connector 25 is formed by a non-deformable cylinder. For example, the non-deformable cylinder 25 presents a diameter equal to the diameter of the tip connector 11. Therefore, when the tip connector 11 is slid along the non-deformable cylinder 25, the tip connector 11 deforms itself.

Thanks to the tip connector 11 and the probe housing connector 25, the operator can chose the type of interchangeable tip that he wanted to use. The interchangeable tip 1 that the operator may use depends of the body morphology. For example, whether the body morphology is obese, then the operator may choose the interchangeable tip 1 equipped with an ultrasound transducer 2 of 2.5 MHz center frequency.

In a non-limiting embodiment, the interchangeable tip 1 comprises a first magnet 12 constructed and configured to cooperate with a second magnet 26 of the ultrasound probe housing 20. In this case and as depicted in FIG. 1, the ultrasound probe housing 20 comprises a second magnet 26. The first magnet 12 and the second magnet 26 exerts an attractive force between the interchangeable tip 1 and the ultrasound probe housing 20 to prevent the interchangeable tip 1 to be expulsed during an examination. The first magnet 12 or the second magnet 26 may also be replaced by a steel part. In this non-limiting embodiment, the tip connector 11 comprises a diameter smaller than the diameter of the probe housing connector 25.

Using one or two magnets in the interchangeable tip 1 or in the ultrasound probe housing 20 present several advantages.

First, if spring-loaded electrical connectors 5 are used, it can compensate the force exerted by the springs. If the interchangeable tip 1 contains four contacts of 0.5 N each, the magnet will have to exert a force of at least 2 Newtons to keep an electrical contact.

Second, as the interchangeable tip 1 is subjected to acceleration (i.e. the acceleration may be generated by an electrodynamic actuator in order to generate shearing waves through the biological tissue), the magnet will maintain the interchangeable tip 1 secured with the ultrasound probe housing 20. Typical acceleration is 0.3 m/s$^2$ for a sinusoidal displacement of 2 mm peak-to-peak amplitude at 50 Hz. If the interchangeable tip 1 mass is 0.03 Kg, the magnet will have to exert a force of at least 0.01 Newton.

In a non-limiting embodiment, the ultrasound probe housing 20 comprises a membrane 28 located at the distal end. The membrane 28 is suitable to be in contact of the skin of the patient during an examination.

In a non-limiting embodiment, the interchangeable tip 1 comprises a first keying device 13 constructed and configured to cooperate with a second keying device 27 of the ultrasound probe housing 20. In a non-limiting embodiment, the first keying device 13 is an orifice located on the intern periphery of the interchangeable tip 1 and parallel to the interchangeable tip 1 longitudinal axis X1. Besides, the second keying device 27 is a pin located in the intern periphery of the ultrasound probe housing 20 and parallel to the ultrasound probe housing longitudinal axis X20. Therefore, when the interchangeable tip 1 is slid along the ultrasound probe housing 20, the pin is slid into the orifice such a manner there is only one possibility to position the interchangeable tip 1. This is advantageous for making an electrical connection between the electrical connectors 5 of the interchangeable tip 1 and the electrical contacts 22 of probe located in the ultrasound probe housing 20.

Figure 4:
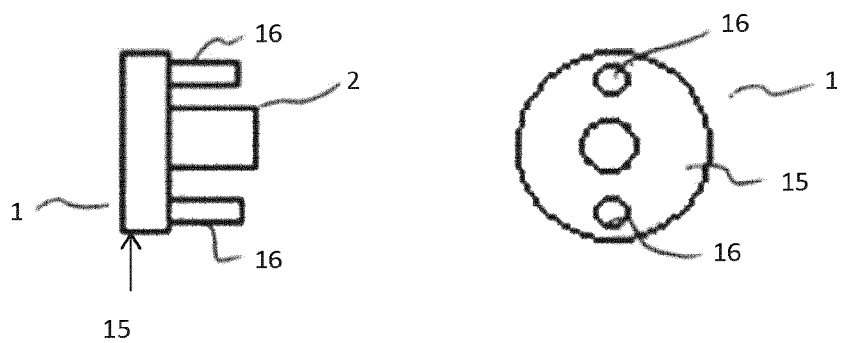
FIG. 4 depicts an interchangeable tip according to the invention comprises centering means.

In a non-limiting embodiment represented in FIG. 4, the interchangeable tip 1 comprises centering means 14 adapted and constructed and configured to center the interchangeable tip 1 between ribs. The centering means 14 may be formed by a ring 15 comprising two locating posts 16 provided on either side of the ultrasound transducer 2. More particularly, when the ultrasound transducer 2 is placed against the thoracic cage, the locating posts 16 of the ring 15 are such that they takes position in the space formed between two adjacent ribs, thus placing the distal end of the ultrasound transducer 2 in the intercostal space. In a non-limiting embodiment, the ring 15 may also form the first magnet.

Figure 5:
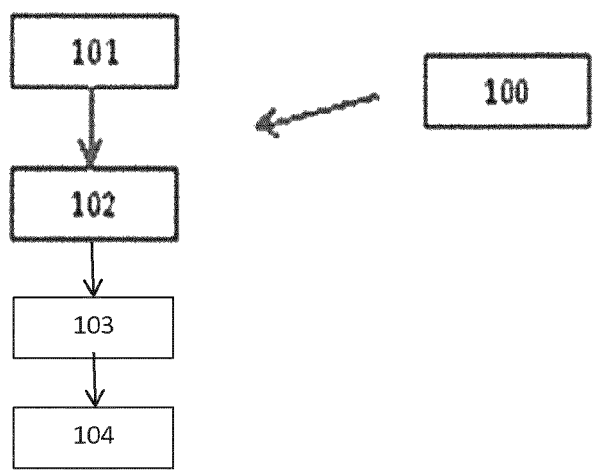
FIG. 5 depicts a method of embodying an ultrasound probe according to the invention.

Another aspect of the invention illustrated in FIG. 5 relates to a method 100 of embodying an ultrasound probe 40 according to the invention.

When an interchangeable tip 1 is secured to the ultrasound probe housing 20, the method comprises a first step 101 of identifying the interchangeable tip 1 by reading the content of the storing means 6,7 of the interchangeable tip 1, the reading being realized by the reading means 23 of the ultrasound probe housing 20, Once the storing means 6,7 are read, the method 100 comprises a second step 102 of selecting acquisition parameters accordingly. The acquisition parameters selected may be formed by the measurement depths, the ultrasound frequency, the shear wave excitation frequency, the shear wave excitation amplitude or others. The selection (called also reprogramming) may be realized by the processor 30 communicating with the ultrasound probe housing 20. In another embodiment, the processor 30 is located into the ultrasound probe housing 20.

Therefore, during an examination, the reading means 23 periodically scans the storing means 6,7 to identify 101 the model of interchangeable tip 1 that is placed on the ultrasound probe housing 20 (or the absence of interchangeable tip 1, and then reprogram the acquisition parameters accordingly.

The method 100 comprises also a third step 103 of freezing the acquisition when the interchangeable tip 1 is removed from the ultrasound probe housing 20. In other words, when the interchangeable tip 1 is removed from the ultrasound probe housing 20 during an examination, the absence of an interchangeable tip 1 is identified by reading the content of the storing means 6,7 of the interchangeable tip 1 which is absent, the acquisition is then freezed 103, then the first step starts again.

The method 100 may also comprises a further step of stopping 104 the work of the interchangeable tip 1 when a tip operation threshold is reached by the interchangeable tip 1. The threshold may be based on tip operation chosen from the list of number of low-frequency impulse, duration of operation or any combination thereof.

According to an embodiment of the invention, the processor 30 and/or the ultrasound probe housing 20 and/or the interchangeable tip 1 may each include one or more processors executing one or more sequences of one or more instructions contained in a memory to perform their intended functions (carry out measurements, collect information, send information, . . . ). In alternative embodiments, hardwired circuitry may be used in place of or in combination with software instructions to implement the invention. Thus, embodiments of the invention are not limited to any specific combination of hardware circuitry and software.

It is to be understood that the present invention contemplates that, to the extent possible, one or more features of any embodiment can be combined with one or more features of any other embodiment.

The descriptions above are intended to be illustrative, not limiting. Thus, it will be apparent to one skilled in the art that modifications may be made to the invention as described without departing from the scope of the claims set out below.

The invention claimed is:

1. An ultrasound probe comprising an interchangeable tip, a magnet, and an ultrasound probe housing,
wherein said interchangeable tip comprises:
at least one ultrasound transducer constructed and configured to emit and receive ultrasound signals,
at least one electrical contact of tip, said at least one electrical contact of tip being constructed and configured to cooperate with an electrical connector,
a tip connector constructed and configured to cooperate with the interchangeable tip with the ultrasound probe housing,
wherein said ultrasound probe housing comprises:
a probe housing connector in a form of an opening, the probe housing connector constructed and configured to cooperate with the tip connector of the interchangeable tip such that, when the probe housing connector cooperates with the tip connector, the tip connector is inserted in the opening and the opening entirely surrounds a portion of an external surface of the interchangeable tip,
at least one electrical contact of probe adapted to contact the electrical connector when said probe housing connector cooperates with the tip connector of the interchangeable tip, and
an electrodynamic actuator constructed and configured to cooperate with the at least one ultrasound transducer, said electrodynamic actuator being adapted to generate a low-frequency impulse having a frequency range between about 1 Hz and about 5000 Hz, and
wherein said magnet is configured to provide an attractive force between the interchangeable tip and the ultrasound probe housing and directed parallel to a longitudinal direction of the interchangeable tip and the ultrasound probe housing, said attractive force being selected such that, solely via said magnet, both the interchangeable tip is retained in the ultrasound probe housing and electrical contact is maintained between the tip connector of the interchangeable tip and the at least one electrical contact of probe when the tip connector of the interchangeable tip is inserted into the opening of the probe housing connector and the electrodynamic actuator generates said low-frequency impulse, said magnet being arranged
in a lowermost surface of the interchangeable tip that contacts a bottommost surface of the opening of the probe housing connector when the interchangeable tip cooperates with the ultrasound probe housing, or
in the bottommost surface of the opening of the probe housing connector.

2. The ultrasound probe according to claim 1, wherein the interchangeable tip is constructed and configured to embed at least one electronic component connected to the at least one electrical contact of tip suitable to cooperate with the electrical connector.

3. The ultrasound probe according to claim 2, wherein the electronic component is a memory suitable to store data relative to the interchangeable tip.

4. The ultrasound probe according to claim 2, wherein the electronic component is a RFID chip suitable to store an interchangeable tip identity information.

5. The ultrasound probe according to claim 2, wherein the electronic component is an acceleration sensor.

6. The ultrasound probe according to claim 1, wherein the interchangeable tip comprises the magnet constructed and configured to cooperate with the ultrasound probe housing.

7. The ultrasound probe according to claim 1, wherein the interchangeable tip comprises a first keying device constructed and configured to cooperate with a second keying device of an ultrasound probe housing.

8. The ultrasound probe according to claim 7, wherein the ultrasound probe housing comprises the second keying device constructed and configured to cooperate with the first keying device of the interchangeable tip.

9. The ultrasound probe according to claim 1, wherein the ultrasound probe housing comprises the magnet constructed and configured to cooperate with the interchangeable tip.

10. The ultrasound probe according to claim 1, comprising at least one processor.

11. The ultrasound probe according to claim 10, wherein the ultrasound probe housing comprises a reading system implemented by electronic components on a circuit board and constructed and arranged to communicate with the processor.

12. The ultrasound probe according to claim 11, wherein the reading system is configured to scan a memory and/or a RFID chip and to transmit data relative to the interchangeable tip and/or interchangeable tip identity information to the processor.

13. The ultrasound probe according to claim 12, wherein the processor selects at least one acquisition parameter according to data retrieved from the memory or the RFID chip.

14. The ultrasound probe according to claim 13, wherein the at least one acquisition parameter is chosen from a list comprising the following parameters: a measurement depth, an ultrasound frequency, a shear wave excitation frequency, a shear wave excitation amplitude.

15. The ultrasound probe according to claim 1, wherein the interchangeable tip cooperates with the ultrasound probe housing via the interchangeable tip connector and the ultrasound probe housing connector.

16. The ultrasound probe according to claim 1, wherein the electrical connector is connected at a first end to the electrical contact of the tip and at a second end to an electrical contact of the probe housing.

17. The ultrasound probe according to claim 1, wherein the electrical connector is a spring-loaded connector.

18. The ultrasound probe according to claim 1, wherein the electrical connector is a jack-like cylindrical connector.

19. The ultrasound probe according to claim 1, wherein the electrical connector is a spring-loaded connector and wherein the attractive force provided by the magnet is sufficient to compensate a spring force exerted by the spring-loaded connector when the interchangeable tip cooperates with the tip connector of the interchangeable tip.

20. A method of embodying an ultrasound probe according to claim 1, the method comprising:
when the interchangeable tip is secured to the ultrasound probe housing, a step of identifying the interchangeable tip by reading a content of a memory and/or a RFID chip, the reading being carried out by a circuit implemented in the ultrasound probe housing,
when the interchangeable tip secured to the ultrasound probe housing is identified, a step of selecting acquisition parameters, the selection being implemented by a processor communicating with the ultrasound probe housing.

21. The method of embodying an ultrasound probe according to claim 20, further comprising when the interchangeable tip is removed from the ultrasound probe housing, a step of freezing acquisition of the acquisition parameters.

22. The method of embodying an ultrasound probe according to claim 20, further comprising when a tip operation threshold is reached by the interchangeable tip, a step of stopping a work of the interchangeable tip.

23. The method of embodying an ultrasound probe according to 20, wherein the acquisition parameters selected by the processor during the step of selecting are chosen from a list comprising the following parameters: a measurement depth, an ultrasound frequency, a shear wave excitation frequency, a shear wave excitation amplitude.

* * * * *